US009658300B1

(12) United States Patent
Weitekamp

(10) Patent No.: US 9,658,300 B1
(45) Date of Patent: May 23, 2017

(54) METHOD AND APPARATUS FOR PREPARATION OF SPIN POLARIZED REAGENTS

(75) Inventor: Daniel P. Weitekamp, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 1752 days.

(21) Appl. No.: 12/543,744

(22) Filed: Aug. 19, 2009

Related U.S. Application Data

(60) Provisional application No. 61/189,418, filed on Aug. 19, 2008.

(51) Int. Cl.
*G01R 33/28* (2006.01)
*A61K 49/18* (2006.01)

(52) U.S. Cl.
CPC ........ *G01R 33/282* (2013.01); *A61K 49/1815* (2013.01)

(58) Field of Classification Search
CPC ............ A61K 49/1806; A61K 49/1815; G01R 33/282
USPC ......................................................... 424/9.3
See application file for complete search history.

(56) References Cited

U.S. PATENT DOCUMENTS

| | | | |
|---|---|---|---|
| 6,278,893 B1 * | 8/2001 | Ardenkjær-Larson et al. | 600/420 |
| 6,466,814 B1 * | 10/2002 | Ardenkjaer-Larsen | A61K 49/08 324/307 |
| 2007/0025918 A1 * | 2/2007 | Hurd | 424/9.34 |
| 2010/0219826 A1 * | 9/2010 | Duckett et al. | 324/307 |

OTHER PUBLICATIONS

Cheng et al., JACS, 2007, 129, p. 139997-14002.*
Knagge et al., J. Phys. Chem. B, 2005, 109, 4533-4538.*
Lisitza et al., J. Chem. Phys., 2009, 131, p. 00508-1-00508-5.*
Macnamara et al., J. Phys. Chem. B, 1999, 103, p. 1158-1160.*
Abragam, A.; Proctor, W. G. *Physical Review* 1958, 109, 1441-1458.
Abragam, A.; Goldman, M. *Reports on Progress in Physics* 1978, 41, 395-467.
Ardenkjaer-Larsen, J. H.; Fridlund, B.; Gram, A.; Hansson, G.; Hansson, L.; Lerche, M. H.; Servin, R.; Thaning, M.; Golman, K. *Proc Natl Acad Sci U S A* 2003, 100, 10158-63.
Ayers GP, Pullin ADE. Nuclear spin conversion of H2O and D2O in argon matrices. Berichte Der Bunsen-Gesellschaft—Physical Chemistry Chemical Physics 1978; 82:62-3.
Bhattacharya, P.; Weitekamp, D. P.; Harris, K.; Lin, A. P.; Ross, B. D. *European Society of Magnetic Resonance in Medicine and Biology* 2004.
Bhattacharya, P.; Harris, K.; Lin, A. P.; Mansson, M.; Norton, V. A.; Perman, W. H.; Weitekamp, D. P.; Ross, B. D., "Ultrafast three dimensional imaging of hyperpolarized 13C in vivo", *Magnetic Resonance Materials in Physics Biology and Medicine* 2005, 18, 245-256.
Bowers, C. R.; Weitekamp, D. P. *Physical Review Letters* 1986, 57, 2645-2648.
Bowers, C. R.; Weitekamp, "Parahydrogen and Synthesis Allow Dramatically Enhanced Nuclear Alignment", D. P. *Journal of the American Chemical Society* 1987, 109, 5541-5542.
Bowers, C. R.; Long, H. W.; Pietrass, T.; Gaede, H. C.; Pines, A. *Chemical Physics Letters* 1993, 205, 168-170.
Bowers, "Sensitivity Enhancement Utilizing Parahydrogen"; Encyopedia of Nuclear Magnetic Resonance, vol. 9, Advances in NMR, 2002, pp. 750-770
Bunkin AF, Nurmatov AA, Pershin SM, Vigasin AA. Four-photon coherent spectroscopy of orientational motion of H2O molecules in liquid water. Journal of Raman Spectroscopy 2005;36(2):145-7.
Bunkin AF, Pershin SM, Nurmatov AA. Four-photon laser spectroscopy of solids in 0-0.15 THz. Laser Physics Letters 2006;3(4):181-4.
Bunkin AE, Pershin SM, Nurmatov AA. Four-photon spectroscopy of ortho/para spin-isomer H2O molecule in liquid water in submillimeter range. Laser Physics Letters 2006; 3(6):275-7.
Carson PJ, Bowers CR, Weitekamp DP. The PASADENA effect at a solid surface: High-sensitivity nuclear magnetic resonance of hydrogen chemisorption. Journal of the American Chemical Society 2001;123(47):11821-2.
M. Carravetta, and M.H. Levitt, Long-Lived Nuclear Spin States in High-Field Solution NMR. *Journal of the American Chemical Society 2004* 126, 6228-6229.
Chapovsky "Enrichment of nuclear spin isomers by molecular coherent control", Institute of Automation and Electrometry, Russian Academy, *Riken Review*, 2002, 44, 30-33.
Cherubini, A.; Payne, G. S.; Leach, M. O.; Bifone, A. *Chemical Physics Letters* 2003, 371, 640-644.
Driehuys, B.; Cates, G. D.; Happer, W.; Mabuchi, H.; Saam, B.; Albert, M. S.; Wishnia, A. *Physics Letters A* 1993, 184, 88-92.
Driehuys, B.; Cates, G. D.; Miron, E.; Sauer, K.; Walter, D. K.; Happer, W. *Applied Physics Letters* 1996, 69, 1668-1670.
Fajardo et al. Matrix isolation spectroscopy of H2O, D2O, and HDO in solid parahydrogen. Journal of Molecular Structure 2004;695:111-27.

(Continued)

*Primary Examiner* — Michael G. Hartley
*Assistant Examiner* — Leah Schlientz
(74) *Attorney, Agent, or Firm* — Kilpatrick Townsend & Stockton, LLP

(57) ABSTRACT

Hyperpolarized samples (i.e., samples having fractional spin polarization P of at least 0.1) of a target molecular species are created through spin transfer from hyperpolarized xenon atoms or other source isotopes. Reversible nanoscale solid state contact is achieved between the hyperpolarized xenon atoms and molecules of a target species. The resulting solid state mixture is exposed to conditions of magnetic field and temperature designed to allow or even facilitate transfer of spin polarization from the xenon to the target molecules. The xenon and the target species are then separated under conditions that substantially preserve the polarization of the target species. The hyperpolarized target species can then be introduced into a subject of a nuclear magnetic resonance (NMR) experiment.

22 Claims, 5 Drawing Sheets

(56) References Cited

OTHER PUBLICATIONS

Fitzgerald, R. J.; Sauer, K. L.; Happer, W. *Chemical Physics Letters* 1998, 284, 87-92.

Frydman, L.; Scherf, T.; Lupulescu, A. *Proceedings of the National Academy of Sciences of the United States of America* 2002, 99, 15858-15862.

H. Gaede, *NMR of surfaces and interfaces using spin polarized xenon.* Ph.D. thesis, Chemistry, University of California, Berkeley, 1995.

Gatzke, M.; Cates, G. D.; Driehuys, B.; Fox, D.; Happer, W.; Saam, B. *Physical Review Letters* 1993, 70, 690-693.

Gerhard, P.; Koch, M.; Jansch, H. J. *Comptes Rendus Physique* 2004, 5, 297-304.

Glasel JA. Near-infrared absorption spectra of ortho-and para-H2O in solid xenon and argon. Journal of Chemical Physics 1960;33(1):252-5.

Goldman et al. "Conversion of a proton pair para order into C-13 polarization by rf irradiation, for use in MRI", Comptes Rendus Physique 2005;6(4-5):575-81.

Goldman, M.; Johannesson, H.; Axelsson, O.; Karlsson, M, "Hyperpolarization of C-13 through order transfer from parahydrogen: A new contrast agent for MRI", *Magnetic Resonance Imaging* 2005, 23, 153-157.

Goldman et al. Design and implementation of C-13 hyperpolarization from para-hydrogen, for new MRI contrast agents. Comptes Rendus Chimie 2006;9(3-4):357-63.

Golman et al. Parahydrogen-induced polarization in imaging: Subsecond C-13 angiography. Magnetic Resonance in Medicine 2001;46(1):1-5.

Golman, K.; Ardenkjaer-Larsen, J. H.; Svensson, J.; Axelsson, O.; Hansson, G.; Hansson, L.; Johannesson, H.; Leunbach, I.; Mansson, S.; Petersson, J. S.; Pettersson, G.; Servin, R.; Wistrand, L. G. *Academic Radiology* 2002, 9 Suppl 2, S507-10.

Golman, K.; Ardenaer-Larsen, J. H.; Petersson, J. S.; Mansson, S.; Leunbach, I. *Proceedings of the National Academy of Sciences of the United States of America* 2003, 100, 10435-10439.

Golman, K.; in't Zandt, R.; Lerche, M.; Pehrson, R.; Ardenkjaer-Larsen, J. H. *Cancer Research* 2006, 66, 10855-10860.

Golman, K.; in't Zandt, R.; Thaning, M., "Real-Time Metabolic Imaging", *Proceedings of the National Academy of Sciences of the United States of America* 2006, 103, 11270-11275.

Haake, M.; Goodson, B. M.; Laws, D. D.; Brunner, E.; Cyrier, M. C.; Havlin, R. H.; Pines, A. *Chemical Physics Letters* 1998, 292, 686-690.

Happer, W. *Reviews of Modern Physics* 1972, 44, 169-250.

Happer, W.; Miron, E.; Schaefer, S.; Schreiber, D.; Vanwijngaarden, W. A.; Zeng, X. *Physical Review A* 1984, 29, 3092-3110.

Hartmann, S. R.; Hahn, E. L. *Physical Review* 1962, 128, 2042-2053.

Ishii, M.; Emami, K.; Kadlecek, S.; Petersson, J. S.; Golman, K.; Vahdat, V.; Yu, J. S.; Cadman, R. V.; MacDuffie-Woodburn, J.; Stephen, M.; Lipson, D. A.; Rizi, R. R. *Magnetic Resonance in Medicine* 2007, 57, 459-463.

Johansson, E.; Mansson, S.; Wirestam, R.; Svesson, J.; Petersson, S.; Golman, K.; Stahlberg, F. *Magnetic Resonance in Medicine* 2004, 51, 464-472.

Johannesson, H.; Axelsson, O.; Karlsson, M., "Transfer of parahydrogen spin order into polarization by adiabatic field cycling." 2004, 5, 315-324.

Joo, C. G.; Hu, K. N.; Bryant, J. A.; Griffin, R. G. *Journal of the American Chemical Society* 2006, 128, 9428-9432.

Knozinger E, Wittenbeck R. Intermolecular Motional Degrees of Freedom of H2O and D2O Isolated in Solid Gas Matrices. Journal of the American Chemical Society 1983;105(8):2154-8.

Konyukhov VK, Tikhonov VI. Adsorption of water molecules on a cluster surface in weak magnetic field under NMR conditions for protons. Bulletin of the Lebedev Physics Institute 1995(1):9-14.

Konyukhov VK, Logvinenko VP, Tikhonov VI. Water separation into sin-modifications and determination of spin-conversion time for a water molecule. Bulletin of the Lebedev Physics Institute 1995(6):31-4.

J.S. Lee, and A.K. Khitrin, Adiabatic cross-polarization via intermediate dipolar-ordered state. *Journal of Magnetic Resonance* 2005, 177, 152-154.

Long, H. W.; Gaede, H. C.; Shore, J.; Reven, L.; Bowers, C. R.; Kritzenberger, J.; Pietrass, T.; Pines, A.; Tang, P.; Reimer, J. A. *Journal of the American Chemical Society* 1993, 115, 8491-8492.

Malyugin et al. "Ratio measurement of water ortho/para nuclear spin isomers via TDLS in the vicinity of 1.92 µ".

Natterer J, Schedletzky O, Barkemeyer J, Bargon J, Glaser SJ. Investigating catalytic processes with parahydrogen: Evolution of zero-quantum coherence in AA ' X spin systems. Journal of Magnetic Resonance 1998;133(1):92-7.

Navon, G.; Song, Y. Q.; Room, T.; Appelt, S.; Taylor, R. E.; Pines, A. *Science* 1996, 271, 1848-1851.

Pines, A.; Gibby, M. G.; Waugh, J. S. *Journal of Chemical Physics* 1973, 59, 569-590.

Potekhin et al. "Spin-dependent absorption of water molecules", Biophysical Chemistry, 2005, v. 118, pp. 84-87.

Redington et al. "Infrared Spectroscopic Evidence for Rotation of Water Molecule in Solid Argon" Journal of Chemical Physics 1962;37(10):2162-2166.

Ruset, I. C.; Kettel, S.; Hersman, F. W. *Experimental NMR Conference,* Asilomar, California 2004.

Ruset, I. C.; Ketel, S.; Hersman, F. W. *Physical Review Letters* 2006, 96.

Ruth, U.; Hof, T.; Schmidt, J.; Fick, D.; Jansch, H. J. *Applied Physics B—Lasers and Optics* 1999, 68, 93-97.

Sauer, K. L.; Fitzgerald, R. J.; Happer, W. *Chemical Physics Letters* 1997, 277,153-158.

Tikhonov et al. "Separation of water into its ortho and para isomers" Science 2002;296(5577):2363.

Walker, T. G.; Happer, W. *Reviews of Modern Physics* 1997, 69, 629-642.

Wigglesworth et al. "Calculated spin-spin coupling surfaces in the water molecule; prediction and analysis of J(O, H), J(O, D) and J(H, D) in water isotopomers" Molecular Physics 1998;94(5):851-62.

Zook, A. L.; Adhyaru, B. B.; Bowers, C. R. *Journal of Magnetic Resonance* 2002, 159, 175-182.

\* cited by examiner

METHOD AND APPARATUS FOR PREPARATION OF SPIN POLARIZED REAGENTS

CROSS-REFERENCES TO RELATED APPLICATIONS

This application claims the benefit of U.S. Provisional Application No. 61/189,418 entitled "Methods and Apparatus For Efficient And General Preparation Of Spin Polarized Reagents", filed on Aug. 19, 2008, the disclosure of which is incorporated herein by reference in its entirety.

BACKGROUND OF THE INVENTION

The present invention relates generally to spin-order transfer and in particular to methods and apparatus for preparation of spin-polarized reagents. Such reagents can be used, for example, in nuclear magnetic resonance (NMR) experiments. The methods and apparatus described herein can be applied to any reagent of biological interest and provide hyperpolarized samples of the reagent as described below.

Since the inception of NMR over sixty years ago, the basic strategy of the vast majority of experiments is unchanged. The sample is placed in the highest available homogeneous field, spin-lattice relaxation allows attainment of the weak equilibrium alignment of the nuclear spins (e.g., a fractional polarization $P=10^{-5}$ for carbon-13 ($^{13}C$) in a magnetic field of 1.5 tesla (T) at room temperature), and Faraday-law inductive detection is used to detect the precessing magnetization induced at the Larmor frequency of the target spins by radio-frequency (RF) irradiation. Despite the sensitivity improvements due to the separate linear increases of both polarization and induced voltage with magnetic field, the fact remains that all routine experiments are performed with polarizations at the part-per-million polarization level. The result is that for the great majority of situations in biology, where the noninvasiveness and chemical specificity of NMR would seemingly make it the method of choice, NMR is instead impractical due to low sensitivity.

For essentially all NMR and MRI experiments in use, the sensitivity is proportional to the fractional polarization P of the target spins. It is remarkable that NMR has contributed so much to our understanding of the brain and other organs using only part-per-million polarizations. That MRI is possible at all is due to slight variations in the density or relaxation times of the highly concentrated (~80 M) water protons. The in vivo study of metabolism with $^{1}H$ or $^{13}C/^{15}N$ NMR with equilibrium spin polarization has been possible only with little or no spatial localization and prolonged signal averaging that largely precludes the study of dynamics and is severely limited by cost. Thus, there has been considerable interest in finding ways to increase the fractional polarization in target molecular species of biological interest.

For example, the PASADENA method (see, e.g., [1][2][3]) can be used to hyperpolarize molecules that can be formed by molecular addition of dihydrogen. PASADENA is unique in achieving nuclear spin polarizations of order unity within seconds at liquid-state temperatures [3][4][5][6][7]. Studies of biological applications of this method are underway. However, for the great majority of molecules of interest as metabolites, drugs, or biopolymers, PASADENA is inapplicable for lack of suitable chemistry.

Another method, dynamic nuclear polarization (DNP), uses electron spin resonance (ESR) irradiation of paramagnetic impurities at temperatures of a few K [8]. DNP methods have recently been improved, and the hyperpolarized products can be rapidly warmed and dissolved for liquid-state studies [5][9][10][11][12][13][14]. Polarization of $^{13}C$ and $^{15}N$ sites in several small molecules has been reported, and in principle this method is generally applicable. In order to reach fractional polarizations of order unity, the sample must be irradiated with microwaves in a dedicated high field magnet (>3 T) at a temperature of about 2 K for several hours prior to rapid melting and dissolution. Nevertheless, the technology has been commercialized, and its success is an indication of the wide recognition in the biomedical community of the potential for hyperpolarized MRI. Of particular interest as a proof of principle for metabolic imaging are the in vivo observation of several hyperpolarized daughter metabolites of $^{13}C$-labeled pyruvate [11][12] and their variation in rate of production with disease state.

BRIEF SUMMARY OF THE INVENTION

The recent successes of the PASADENA and DNP methods have set a high bar for new hyperpolarization methods. They must not only be capable of delivering comparable or better spin polarizations into aqueous solutions, but must have other advantages, such as throughput, cost, and sample purity. These issues are among those addressed by embodiments of the present invention.

Embodiments of the present invention provide methods and apparatus for creating hyperpolarized samples of a target molecular species through spin transfer from hyperpolarized xenon (Xe) atoms. The target species can include a variety of species relevant to biomedical magnetic resonance imaging (MRI). Hyperpolarized xenon, in particular the isotope $^{129}Xe$ can be produced using existing techniques. In an embodiment of the present invention, reversible nanoscale solid-state contact is achieved between the hyperpolarized xenon atoms and molecules (including single-atom molecules) of a target species. The resulting solid-state mixture is created under conditions of magnetic field and temperature designed to allow or even facilitate transfer of spin polarization from the xenon to the target molecules. During the spin-transfer process, solid-state NMR can be used to measure the polarization of both the $^{129}Xe$ and the target species (e.g., $^{13}C$, $^{15}N$, $^{1}H$), as an aid to optimizing the polarization dynamics and the resulting spin polarization of the target species. The xenon and the target species are then separated under conditions that substantially preserve the polarization of the target species. The target can be dissolved in aqueous solution either during or after separation from the xenon and introduced into a subject of an NMR experiment.

By providing the potential for a wide range of hyperpolarized target species to be used in NMR experiments in living subjects, the present invention opens up an entirely new regime wherein the local status of metabolism, drug delivery and other dynamic processes can be interrogated on the time scale of seconds to minutes with unprecedented chemical specificity.

Certain embodiments relate to methods and apparatus for preparing target molecules in a hyperpolarized state. The methods can include creating a solid nanoscale mixture of hyperpolarized source isotopes with target molecules of a target molecular species, inducing a transfer of spin order from the hyperpolarized source isotopes to the target molecules within the solid mixture, thereby establishing a hyperpolarized state of the target molecules, then removing the hyperpolarized source isotopes from the mixture while maintaining the target molecules in the hyperpolarized state. A variety of specific techniques and apparatus can be used for creating such a mixture and inducing the spin order transfer.

Certain other embodiments relate to methods and apparatus for preparing target molecules in a hyperpolarized state using an intermediate surface. For example, the surface can include surface molecules having a spin and a slow spin lattice relaxation rate. Hyperpolarized xenon (or other highly spin-polarized source molecules) can be applied to the surface, after which a transfer of spin order from the hyperpolarized xenon to the surface molecules can be induced. The xenon can be removed from the surface while preserving the spin order of the surface molecules, after which target molecules of a target molecular species can be applied to the surface and a further a transfer of spin order from the surface molecules to the target molecules can be induced. A variety of specific techniques and apparatus can be used.

Certain other embodiments relate to methods and apparatus for conducting a nuclear magnetic resonance (NMR) experiment on a subject. For example, starting with a nanoscale mixture of target molecules of a target molecular species and hyperpolarized source isotopes in a solid state, a transfer of spin order from the hyperpolarized source isotopes to the target molecules can be induced, thereby establishing the target molecules in a hyperpolarized state. The source isotopes can be separated from the hyperpolarized target molecules, and the hyperpolarized target molecules into the subject. Thereafter, an NMR measurement can be performed on the subject, and the NMR measurement can include detecting a signal corresponding to an isotope included in the target molecular species.

The following detailed description together with the accompanying drawings will provide a better understanding of the nature and advantages of the present invention.

DETAILED DESCRIPTION OF THE INVENTION

Figure 1:
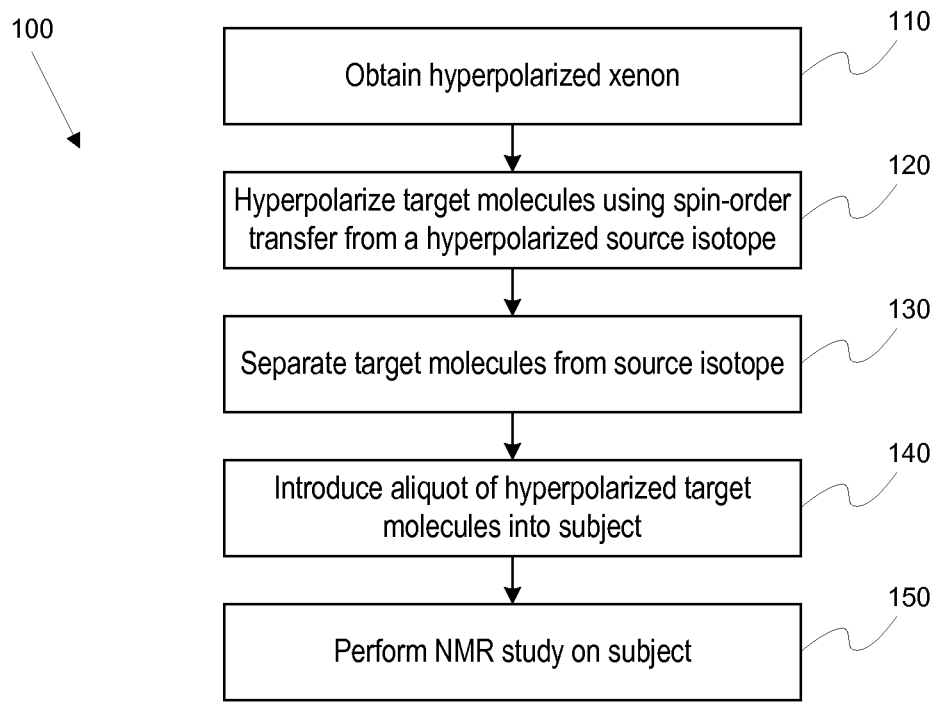
FIG. 1 is a flow diagram of a process for NMR studies according to an embodiment of the present invention.

Embodiments of the present invention provide techniques and apparatus for creating hyperpolarized samples (i.e., samples having fractional spin polarization P of at least 0.1) of a target molecular species through spin transfer from hyperpolarized xenon (Xe) atoms. The target species can include a variety of species relevant to biomedical magnetic resonance imaging (MRI) and other NMR experiments. Hyperpolarized xenon, in particular the isotope $^{129}$Xe can be produced using existing techniques. In an embodiment of the present invention, reversible nanoscale solid-state contact is achieved between the hyperpolarized xenon atoms and molecules (including single-atom molecules) of a target species. The resulting solid-state mixture is created under conditions of magnetic field and temperature designed to allow or even facilitate transfer of spin polarization from the xenon to the target molecules. During the spin-transfer process, solid-state NMR can be used to measure the polarization of both the $^{129}$Xe and the target species (e.g., $^{13}$C, $^{15}$N, $^1$H), as an aid to optimizing the polarization dynamics and the resulting spin polarization of the target species. The xenon and the target species are then separated under conditions that substantially preserve the polarization of the target species. The target can be dissolved in aqueous solution either during or after separation from the xenon and introduced into a subject of an NMR experiment.

Embodiments of the present invention can facilitate NMR studies by increasing the fractional polarization of the target species in the subject of study. In this aspect, the strategy is to "hyperpolarize" target molecules to fractional polarization P>0.1 and then insert them into the environment of interest (e.g., a tissue of a living subject) prior to the NMR or MRI study. This strategy is necessary because no effective general method of in situ hyperpolarization is available for the environment of greatest interest for applications, such as liquid solutions. This strategy is possible because the time scale for which spins remain hyperpolarized is the familiar spin-lattice relaxation time $T_1$ (typically 1-100 seconds in liquids), long enough for many species to enter tissues and cells and even to undergo biochemical reactions, during which the spin state is conserved.

Using techniques described herein, the polarization enhancements achievable at the time of entry to the in vivo environment are, for example, a factor of order $10^4$. By way of comparison, to achieve the same sensitivity in an NMR measurement without this enhancement would require $10^8$ repetitions, a minimum of $10^8$ s or 3 years. Hyperpolarization therefore not only vastly increases the time resolution and the rate at which NMR data of adequate sensitivity is collected but also enables studies on small and low density populations of molecules which would be entirely impractical without it. Even after 5 $T_1$ (several minutes for favorable nuclear sites in solution) the available signal is still more than 2000 times greater than the equilibrium $^{13}$C signal at 1.5 T, the field of most human MRI instruments. Thus, there is time for the hyperpolarized molecules to be delivered via blood flow, taken up into extracellular and intracellular volumes, and even metabolized before data acquisition. The signal-to-noise ratio after 5 $T_1$ with hyperpolarization would be achieved with ordinary polarization only after more than 50 days of signal averaging at 1 measurement per second. Thus hyperpolarization methods are poised to revolutionize chemically-specific in vivo MRI by making practical a class of observations both broader than and complementary to existing methods. Changes in concentration in the micromolar (μM) regime, occurring in seconds, become observable in single shot experiments over volumes of interest.

Embodiments of the present invention provide approaches to transferring spin polarization between atoms or molecules which can be readily hyperpolarized and arbitrary molecules, especially those of interest for chemical and biological studies. In an illustrative example, one input to a spin-transfer device can be a micromole quantity of the target molecule, typical of the dose needed for in vivo small-animal studies and more than adequate for analytical uses of NMR. The other input is hyperpolarized $^{129}$Xe whose production, by continuous-flow spin-exchange optical pumping, is possible at the polarization and flux needed to realize this example. (In other embodiments, $^3$He or other species that may be available with the necessary abundance and spin polarization can be substituted).

Within the device, the direct dipolar couplings in the solid state between dilute target molecules and abundant $^{129}$Xe are relied on to transfer the hyperpolarization. This approach is advantageously nonspecific; the same procedure polarizes a wide variety of target molecules and even mixtures containing multiple different target molecules in a reproducible manner. The process is also efficient and quantifiable, polarizing the target spins to nearly the same low spin temperature (or high fractional polarization) as that of the initial $^{129}$Xe. It is also possible to polarize multiple sites in the same molecule or different molecules to a predictable level. This allows the signals from different nuclear sites to be used ratiometrically. Achieving high spin order on multiple sites is also a route to enhanced signals for those NMR methods in which the signals are proportional to the correlation, in the initial condition, of the spin order on two or more sites. The spin order so created in the solid state may be substantially preserved through phase transformations and chemical reactions and observed with the full finesse and chemical specificity of high-field NMR, for example in the liquid state. Thus, the output of the spin-transfer device can be a nontoxic, aqueous solution of the target molecule in a volume of approximately 1 milliliter with anticipated spin polarization P~0.1. Specific examples are described below.

All aspects of the method are readily scaled up to the concentrations and volumes needed for human in vivo studies, and products, processes and services incorporating techniques and devices described herein are contemplated. This new capability will enable diverse approaches to diagnosis and treatment monitoring by in vivo magnetic resonance imaging (MRI) as well as new approaches to combinatorial chemistry using NMR for structural and binding studies in pursuit of drug discovery and fundamental understanding of biomolecules.

FIG. 1 is a flow diagram of a process 100 according to an embodiment of the present invention. At step 110, hyperpolarized xenon is obtained. As is known in the art, xenon has nine stable isotopes, seven of which have no nuclear spin. Of particular interest is the spin 1/2 isotope $^{129}$Xe (27.8% natural abundance (n.a.)), which is commercially available at up to 90% enrichment. The spin 1 isotope $^{131}$Xe (21.2% n.a.) can be depleted to levels of less than 1% [15], but when present at the more typical levels it is also relevant to the spin physics of solid xenon [16].

As is also known in the art, the nuclear spins of noble gases can be hyperpolarized by the phenomenon of spin exchange optical pumping [17][18][19]. Circularly polarized light is used to create net electron spin angular momentum in alkali metal atoms (e.g., rubidium), and this is transferred to the noble gas nuclei via transient van der Waals collision complexes. Several groups have reported fractional polarizations of P~0.7 [15][20][21][22] in the $^{129}$Xe isotope after separation from the alkali metal and buffer gases used in the optical pumping step. Of particular interest are flowing systems [21][22][23][24], which have been commercialized. Such conventional systems and methods can be used to produce hyperpolarized xenon for use as described below.

In some embodiments, other species can be substituted for xenon. For example, hyperpolarized $^3$He can be produced using known techniques in sufficient quantities for use in the techniques described herein. As hyperpolarization techniques for other isotopes of noble gases or other atomic or molecular species may be developed in the future, such isotopes may also be used in connection with the techniques herein. Accordingly, certain embodiments described herein may refer generally to a hyperpolarized "source" isotope that acts as a source of spin order that is to be transferred to the target.

At step 120, target molecules are mixed with the hyperpolarized xenon (or other source isotope) and exposed to conditions that allow spin-order transfer from the xenon to the target molecules. In this step, the goal is efficient intermolecular polarization transfer, where the transfer is considered efficient if the target's polarization becomes comparable to the source's (e.g., xenon's) polarization in a time short compared to the spin-lattice relaxation times of both species. Suitable conditions include: creation of a nanoscale mixture of the target molecules with a mole fraction of xenon sufficiently large that the spin temperature of the mixture approaches the initial low spin temperature of the xenon; and a solid-state environment (e.g., freezing the mixture) that allows spin-order transfer through the average dipolar couplings (which does not require molecular motion).

Efficient intermolecular polarization transfer can be achieved in the solid state. Here a variety of efficient mechanisms for polarization transfer are available, including mechanisms mediated by the average dipolar couplings, requiring no molecular motion. The energy gap, characterized by the difference between the Larmor frequencies of the source and target isotope, must be somehow compensated to achieve efficient polarization transfer. This can be achieved with appropriate RF (radio-frequency) pulse sequences in a high magnetic field [25][26][27] or by so-called thermal mixing [28], which entails simply cycling the magnetic field to such low values (less than about 10 mT for the isotope pair $^{129}$Xe and $^{13}$C) that the nonsecular dipolar couplings between neighboring atoms mediate energy exchange on a time scale short compared to spin-lattice processes.

The behavior of nuclear spin magnetization when the field at the sample is reduced and restored on a time scale short with respect to spin-lattice relaxation times is well understood in terms of the spin temperature hypothesis [28]. In the case where the magnetic field is reduced to a value smaller than the local fields of the neighboring spins, the Zeeman spin order of one or more isotopes is converted into dipolar order, the relative ordering of the spins with respect to one another. For a sample at a uniform spin temperature (e.g. initially at equilibrium in high field) this interconversion is isentropic and reversible; the original spin polarization of each isotope in the direction of the field is recovered upon adiabatic restoration of the magnetic field. In the case of interest, where the polarizations of the various isotopes are initially not in the equilibrium ratio, a rapid and irreversible transfer of spin order among all magnetic isotopes in the mixture occurs in low field in a time short compared with any solid-state spin-lattice relaxation time. The various isotopes reach a common spin temperature in an irreversible process at low field. This spin temperature can be readily calculated from the initial spin temperatures and spin heat capacities of the various isotopes. For times short compared to spin-lattice relaxation times, the subsequent evolution to higher and/or lower fields is isentropic and reversible.

Efficient intermolecular polarization transfer appears to be more difficult in a liquid state. In the magnetic fields commonly used for NMR 50 mT), the signals from different isotopes are spectrally well resolved from one another with the corollary that the Zeeman polarization of each species is, to a good approximation, a separate quasiconstant, relaxing toward its own equilibrium value with its own spin-lattice relaxation rate. Cross-relaxation rates between isotopes (e.g. nuclear Overhauser effects), mediated by molecular motion, are measurable in liquids at high fields, but even in hyperpolarized xenon as solvent [29][30][31] are inefficient at transferring spin order between molecular species. In experiments, polarization of the target species to only $P \sim 10^{-4}$ is observed even when they are dissolved in liquid $^{129}$Xe with polarization of $P \sim 10^{-1}$. Further, due to the rapid motion of molecules in liquids, only small improvements in this efficiency might be expected by varying conditions of temperature or magnetic field. Thus, solid state is preferred.

In some embodiments, the target molecules are surrounded by an excess of $^{129}$Xe that has been polarized to order unity by a prior optical pumping procedure, and this mixture is frozen to allow efficient thermal mixing. The initial polarization of all isotopes other than $^{129}$Xe is initially insignificant. Further, in embodiments where hyperpolarized $^{129}$Xe is continually produced and introduced to the target molecules at nearly its peak polarization, only the relaxation times in the cold solid state are relevant to the amount of polarized material that can be produced. Provided that the mixing takes place in a magnetic field high enough that the differences between the Larmor frequencies of the various isotopes is much greater than the linewidths (typically 1-100 kHz) of each isotope species, the various isotopes relax independently; thus, the polarization of the xenon will decay slowly compared to the mixing process.

Spin-order transfer from the xenon to the target also needs to take place quickly relative to the decay time for the xenon polarization. For spin-order transfer, it is the difference in Larmor frequency relative to the dipolar couplings that determines whether the Zeeman energy reservoirs come to the same spin temperature quickly or not. Only when this ratio is much greater than unity will differences in spin temperature persist for times that allow the different isotopes to relax independently. Lowering the applied field so that this ratio is comparable to unity is provides a low field thermal mixing procedure. Alternatively, pulsed methods at high field can be used; these methods involve irradiation at two Larmor frequencies to allow the spin temperature to equilibriate. While the details vary with the target and other conditions, equilibration of spin temperatures in times on the order of 1 ms is routine for spin pairs separated by a few bond lengths (less than about 1 nm).

It should be noted that previous studies of spin-order transfer processes have not achieved efficient hyperpolarization (defined herein as a spin polarization P of the target that is at least half of the value expected on the basis of the spin temperature theory for the method of polarization transfer) for a target species other than $^{131}$Xe and a source species other than $^{129}$Xe. For the exceptional case, polarization of $^{131}$Xe by $^{129}$Xe in bulk solid xenon, agreement with spin temperature theory was quantitative, with P reaching 0.05, more than a third of the initial $^{129}$Xe polarization [16]. This observation confirms the adequacy of spin temperature estimates as a criterion for measuring efficiency of hyperpolarization. However, this case is special in that there is no tendency for a mixture of $^{131}$Xe and $^{129}$Xe to spatially segregate, nor does the target atom disrupt the lattice and increase the degree of motion.

Thermal-mixing polarization of molecules exposed to hyperpolarized $^{129}$Xe has been reported, but the results have not reached the levels of efficiency or polarization of the target contemplated herein. For surface protons of a polymer thin film on glass, polarizations of at least $10^{-2}$ and possibly as high as $10^{-1}$ were achieved [32]. The large uncertainty is associated with the poorly characterized number of protons sharing the spin order. For the conceptually simpler case of freezing gaseous mixtures of a small molecule with xenon, polarizations fell short of the spin temperature predictions by over an order of magnitude [33][34]. The explanation suggested for this result was inadequate mixing or partial recrystallization, presumably resulting in target spins surrounded by other target molecules and too distant from xenon atoms to reach the spin temperature limit [33][34]. This is a plausible explanation for the case of $CO_2$ [33] and $CS_2$ [34] targets, since the diluteness of the magnetic isotopes within these solids would lead to slow spin diffusion if phase separation occurred due to insufficiently rapid freezing. Some embodiments of the present invention provide improvements in mixing and freezing techniques that prevent or minimize phase separation and molecular motions, either or both of which can lead to losses of spin order by excessively fast spin relaxation.

Mixing problems might also be mitigated in organic solids, since these have spin diffusion rates at least as rapid as that of solid Xe ($\sim 10$ nm$^2$/s). Thus, couplings between protons and between protons and dilute isotopes lead to a common spin temperature even in macromolecules or frozen nanoparticles or thin films mixed with $^{129}$Xe on a length scale of <10 nm. The polarizations predicted by spin temperature theory are, at the proton density of organic metabolites, proteins or aqueous solutions, reached in at most several seconds. However, prior attempts to use thermal mixing to polarize organic molecules nominally dispersed in frozen xenon [35] have proven inefficient, indicating that the conditions for nanoscale mixing in a region with spin relaxation time long compared to the time needed for polarization transfer have not been realized.

In summary, the literature results to date are consistent with the hypothesis that a system of hyperpolarized xenon plus an arbitrary target molecule, if prepared in close proximity and cycled to a low magnetic field, will reach high field polarizations which are a large fraction of the initial $^{129}$Xe polarization and are in the proportion of their gyromagnetic ratios, as follows from spin temperature theory. However, the failure to achieve nanoscale mixing and sufficiently long spin-lattice relaxation times has prevented the predicted efficiencies of polarization transfer from being realized for any combination of a target molecule of interest and a hyperpolarized source isotope. Both spin hyperpolarization and nanoscale mixing are nonequilibrium properties, unstable in the presence of thermally activated motions. Prior efforts have evidently failed to control these motions, with the result that nearly all of the spin order initially present is lost in the attempted spin-order transfer and unavailable for the application. The present invention supplies improved methods to achieve this goal for diverse target and source species, in part by mitigating the molecular motions and polarization losses inherent in prior art methods.

One challenge is to achieve "nanoscale mixing" of the target into the xenon, i.e., a mixture in which substantially all (at least 90%) of the target molecules are in close enough proximity to a xenon to allow effective spin diffusion from the xenon to the target. For typical sites within an organic molecule or a complex of molecules in the solid state, "close enough proximity" implies a distance of about 10 nm or less. In such mixtures, a common spin temperature can be achieved via spin diffusion in thermal mixing at low magnetic field or other solid-state polarization transfer mechanisms [25][26][27][36] which are performed at high field. Specific examples of processes and apparatus for achieving nanoscale mixing are described below.

In some embodiments, the hyperpolarized mixture can be prepared in advance and stored under suitable conditions of temperature and magnetic field to slow the spin lattice relaxation rate, thus allowing hyperpolarized samples to be transported from a manufacturing site to an experimental site and/or stored at the experimental site and used over a period of hours or days.

Referring again to FIG. 1, at step 130, the target species is separated from the xenon. This step is advantageously performed near the time of actual use. Since Xe sublimes or melts rapidly at temperatures where nearly all species of interest as targets (e.g., organic metabolites or macromolecules) remain solid with negligible vapor pressure, much of the Xe can be removed (and recycled) at temperatures where the spin-lattice relaxation time $T_1$ of the target nuclei in the oxygen-free solid typically exceeds $10^2$ s. For example, crushing the frozen mixture of Xe and target species can increase the surface area and hasten the removal of much of the Xe by sublimation without substantial loss of spin order. Alternative techniques for removing xenon are described below in connection with specific techniques for forming mixtures.

Once the target is separated from the xenon, the rate of dissipation of spin order may become comparable to the time needed for further sample manipulation and for the NMR itself Spin-lattice relaxation of each isotope is acting to dissipate its own hyperpolarization. These high field spin-lattice relaxation processes are again substantially uncoupled and the lifetime of the spin polarized target molecule is determined, as usual, by its available degree of molecular motion.

At step 140, an aliquot of the target, largely free of xenon, is introduced into the NMR subject. A variety of techniques may be used.

For instance, in some embodiments the solid material containing the hyperpolarized target molecules is the product of interest for the NMR application. This includes applications where the spin order is to be detected in the solid state, as well as other cases where delivery into the subject of the NMR study as a solid is advantageous, even if melting or dissolution within the system is intended before detecting the NMR signals. Advantages of a solid in the context of delivering a hyperpolarized sample into the subject include its high spin density and long spin-lattice relaxation time. Examples of techniques for delivering solids for in vivo applications include inhalation, injection and adsorption through skin or exposed tissue. Any of these techniques may be used, depending on the properties of the target molecule and the location and type of the tissue of interest.

In other embodiments, step 140 can include dissolving the residue of step 130 (consisting largely of the target species) in a solvent appropriate for the desired NMR spectroscopy. The solution can then be introduced to the NMR subject, e.g., by injection, ingestion, or adsorption. Use of a solvent of a quantity and temperature sufficient to melt and dissolve the frozen mixture can also augment or replace xenon collection by sublimation at step 130; any xenon that does not promptly dissolve will bubble out for collection. Further, due to its chemical inertness, residual xenon is typically not problematic, even if some enters the NMR subject along with the target species.

In solution, the liquid-state relaxation times (typically 10 to 100 seconds for targets of interest) apply. Accordingly, spin polarization dissipates more rapidly in solution than in the solid state, and speed of handling is important. For this reason, the solution would typically be created near or in the high field spectrometer. Similar techniques have been used in connection with in vivo studies using samples prepared using DNP and PASADENA [3][4][5][10][37].

At step 150, an NMR experiment is performed on the subject. Conventional NMR techniques may be used. For example, the subject can be placed in a strong magnetic field (e.g., 1.5 T), and a sequence of RF pulses can be applied to induce precession at the Larmor frequency of the target species. Such precession can be inductively detected as in any NMR experiment; however, to the extent that the target species is hyperpolarized, the sensitivity of the measurement is significantly enhanced.

This enhancement does not persist indefinitely. Regardless of the pulse sequence, after an interval several times longer than the $T_1$ of the target spin, the sample must be changed in order to continue observing significantly enhanced signals. If $T_2$ (the spin dephasing relaxation time) is shorter than $T_1$, spin evolution in the target species may deplete the polarization even faster. One practical approach is to prepare multiple hyperpolarized aliquots and automate all or part of the separation and introduction steps, so as to achieve a repetition period of seconds, comparable to the repetition period of ordinary NMR practice.

Despite this constraint, with the use of recently developed pulse sequences, even quite complex NMR studies can be accomplished in a time short compared to $T_1$ and thus with a single hyperpolarized aliquot. For example, using ordinary room-temperature polarization a variety of 2D NMR experiments have been realized in a single transient [38]. The "single-scan" experiment makes use of field gradients to, in effect, use different parts of the NMR tube for different spin evolution periods. With the hyperpolarization methods described herein, this approach can be generalized to more dilute targets.

As another example, in the context of medical MRI, fast imaging methods have recently been applied [3][4][5][6] to in vivo $^{13}C$ imaging of molecules hyperpolarized by improved versions [4][5][6][39] of PASADENA [1][2] or DNP [5][8][9][10]. Thus a single hyperpolarized sample may be used to achieve multiple 2D images in a fraction of a second or even a 3D [3] image. Of particular interest are isotopes such as $^{13}C$ and $^{15}N$, whose spin-lattice relaxation times in the liquid state are typically tens of seconds. Singlet states, describing a relative ordering of two like nuclei, provide a way of storing spin order on a time scale even longer than the spin-lattice relaxation time, but which is interconvertible with spin polarization [40]. Replacement of protons by deuterium can be used to minimize dipolar relaxation, prolonging the time available during which these hyperpolarized spin labeled metabolites and drugs can probe such dynamic processes as chemical speciation, transport, and binding, in vitro or in vivo.

It will be appreciated that the process described herein is illustrative and that variations and modifications are possible. Steps described as sequential may be executed in parallel, order of steps may be varied, and steps may be modified, combined, added or omitted. For example, in one alternative embodiment, a mixture of target molecules and xenon (or other source isotope) can be stored prior to inducing spin order transfer. At the time of an NMR study, an aliquot (desired amount) of the mixture can be removed from the mixture. If the aliquot is briefly (~1 s) cycled to low magnetic field, a uniform spin temperature for all isotopes is reached. Restoration of high field conditions (in or near the NMR magnet) again isolates the various reservoirs of Zeeman spin order associated with different isotopes. Each isotope's high field polarization is then in proportion to its gyromagnetic ratio. In the limit of an excess of $^{129}$Xe, the final common Zeeman spin temperature is close to the initial spin temperature of the $^{129}$Xe at the same field, but now this highly ordered state is shared by all spin-bearing molecules.

Examples of techniques and apparatus for achieving solid-state nanoscale mixtures of xenon with a target molecular species will now be described. It is to be understood that these techniques and apparatus could be adapted to use species other than xenon as a source of hyperpolarization.

Figure 2:
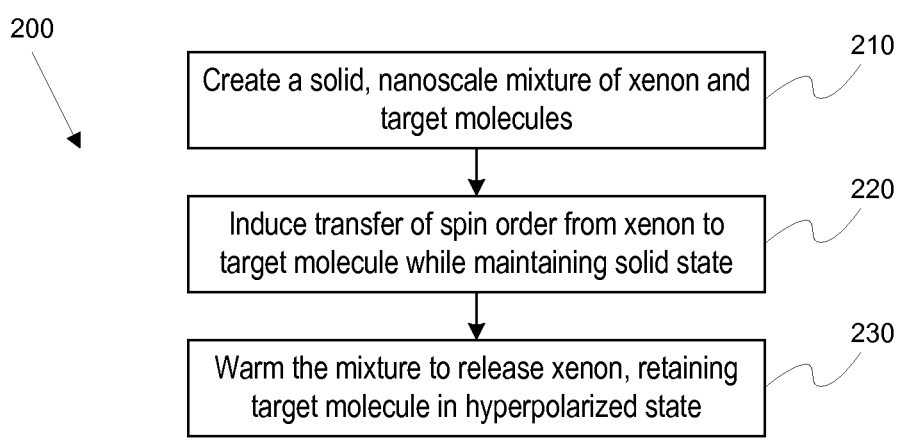
FIG. 2 is a flow diagram of a process for creating a nanoscale mixture and transferring spin order according to an embodiment of the present invention.

FIG. 2 is a flow diagram of a process 200 for creating a nanoscale mixture and transferring spin order according to an embodiment of the present invention. In process 200, a solid nanoscale mixture of hyperpolarized xenon and the target molecules is created at step 210. Mixing can be performed in solid, liquid, or gas phases, and the mixture can subsequently be solidified (frozen), e.g., by rapidly lowering its temperature. Specific examples of processes for creating solid nanoscale mixtures that may be incorporated into process 200 are described below.

A particular ratio of xenon to target molecules is not critical to the present invention. Preferably, the ratio is such that each target molecule is close enough to a $^{129}$Xe to allow efficient spin order transfer through dipolar coupling. In principle, this can be achieved with target concentrations as high as 1:1 (target:xenon), but lower target concentrations, e.g., on the order of 1:10, are preferred. The overall spin temperature of the mixture should approach that of the hyperpolarized xenon, and this advantageous regime requires that the source isotope dominates the mole fraction and that the losses due to spin relaxation are kept small during all steps.

The target species and Xe are advantageously intimately combined in a sufficiently high magnetic field (e.g., above 50 mT) to ensure that the mixing and freezing operations can be carried out with little loss of spin order. Typical values of $T_1$ (spin-lattice relaxation time) for $^{129}$Xe are 3600 s in the gas phase [32], 100 s in the supercritical phase [41], 1200 s in the liquid phase [30][34], and 8500 s in the solid phase at 77 K [16]. Thus, sample manipulations (e.g., mixing with xenon) in any of these phases is practical with little loss of $^{129}$Xe polarization. As long as the freezing takes place in a magnetic field high enough that the isotopes maintain separate reservoirs of Zeeman order, the maximum time allowed for achieving nanoscale mixing and freezing without incurring appreciable losses to the spin order is set by the $T_1$ of $^{129}$Xe itself. As noted, this time is >$10^3$ seconds in both the liquid and solid at the relevant temperature (~77 K), while solidification may be accomplished more quickly.

At step 220, a transfer of spin order from the xenon to the target molecules is induced while the mixture is maintained in the solid state. For example, in some embodiments it is only necessary to lower the magnetic field to make thermal contact between the spin systems of the various isotopes. The details of this step are not critical, since the time scale for reaching a common spin temperature in a near-zero field is much less than 1 s when the mismatch of Zeeman energies is overcome by lowering the magnetic field to a low value.

In other embodiments, the mismatch of Zeeman energies can be overcome by using high-field methods of cross polarization, which also allow the diffusion of Zeeman and/or dipolar spin order.

The overall strategy is to form the solid at step 210 under conditions of sufficiently low temperature that the multinuclear $T_1$, the time constant with which the common reservoir of spin order diminishes, is much longer than the time needed for the spin order to be shared during step 220. To approach the ideal limit in which the target species reaches the spin temperature set by the isotopic composition and the high initial polarization of the abundant hyperpolarized $^{129}$Xe, it is only necessary to avoid maintaining the thermal contact between isotopes so long that dissipation of this shared spin order becomes appreciable. Possible dominant sources of spin-lattice relaxation at temperatures below the melting point of the mixture (typically below the 160 K melting point of xenon) include the quadrupole relaxation of $^{131}$Xe, the dipolar relaxation of any methyl groups that might be present in the target species, and the spin-rotation relaxation of $^{129}$Xe itself. The impact of these processes on the common spin temperature are weighted by the isotopic abundances, which provides a method for diagnosing these losses of spin order, should they prove significant at a given temperature. By lowering the temperature and cycling the field down from greater than 50 mT and back up in about 1 second, a common spin temperature is reached with very small fractional losses of spin order before separate Zeeman reservoirs are established again by the differences in Larmor frequency in even this modest field. Thus the details of the relaxation are not critical, since the temperature is chose to be sufficiently low that the time spent under conditions of spin-order sharing (e.g., fields below 10 mT) is short relative to the relaxation times, which can always be increased by lowering the temperature. The optimum temperature depends on the particular mixture and can be determined experimentally.

Similarly, if methods of transferring spin order in high field are used (see, e.g., [25][26][27][36]), the relevant dissipative time constants (spin-lattice relaxation time, spin-locked relaxation time, high-field dipolar relaxation time) are increased by lowering temperature.

At the higher field (above 50 mT) and subsequently to the polarization transfer at step 220, it is the relaxation time of the target isotope (e.g., $^{13}$C) which sets the timescale for further action. This is expected to be at least several minutes at temperatures where Xe can be removed from the mixture as a liquid or gas (e.g., temperatures above 162 K) and longer at temperatures where the mixture remains in the solid state.

In some embodiments, the mixing and spin-order transfer can take place within an NMR instrument (which supplies not only a high magnetic field but also an RF pulse generator and spectrometry equipment). Solid-state NMR techniques can accordingly be used to measure the polarization of the $^{129}$Xe and/or target isotopes at various stages of the process. In some embodiments, the results of such measurements can be used to tune process parameters (e.g., temperature, magnetic field ramping etc.).

In some embodiments, either before or after transferring spin order at step 220, the mixture can be stored in the solid state until it is ready for use. Storage can take place in a specially prepared container maintained at ultracold temperatures in a strong magnetic field. For example, long term storage of $^{129}$Xe spin order (e.g., with $T_1$>$10^6$ s) has been demonstrated at a temperature of 4.2 K and a field of 0.1 T [16]. If the materials to be mixed with the xenon are purged of oxygen and free of other paramagnetic impurities, relaxation times similar to those in solid xenon may hold for the $^{129}$Xe in a mixture. A small Dewar of liquid He fitted with permanent magnets can sustain the required conditions for hours or days. While such longer term storage is not required, it would (albeit at greater expense in cryogens) allow multiple samples to be prepared together and used over a period of several days.

At step 230, the mixture is warmed to release the xenon, e.g., using dielectric heating or thermal diffusion. In some embodiments, a solvent may also be introduced to create a solution of the target molecule ready for introduction into the subject. This step is advantageously performed near in time (e.g., within seconds or minutes) to introduction of the sample into the NMR subject in order to minimize loss of spin order.

Process 200 can provide speed and throughput advantages over alternative techniques for polarization enhancement. For example, in some embodiments, the fundamental rate processes occur in seconds or less, and the required sample manipulations can in principle take place on this time scale if desirable. This is in contrast to DNP methods, in which the nuclear polarization rate is limited by spin diffusion to the vicinity of paramagnetic impurities and these sites must be kept dilute in order for the asymptotic polarization to be high. It is unlikely that DNP will achieve polarization of order unity for arbitrary target molecules in much less than the time of ~1 hour demonstrated by [9]. In contrast, methods described herein can allow the target species to approach the spin temperature of the abundant $^{129}$Xe in a process that takes no more than a few tens of seconds.

As noted above, a variety of processes can be used to achieve nanoscale mixing of xenon and a target species. Several examples will now be described. These processes are advantageously performed in a high magnetic field such that the xenon and target isotopes maintain separate reservoirs of Zeeman order. Preferably, xenon purified to a high concentration of $^{129}$Xe is used, and the xenon is hyperpolarized, e.g., using existing techniques, prior to mixing with the target species. The mixing operation can be performed in proximity to the source of hyperpolarized xenon to reduce the degradation of spin order that would be expected over time. Generation of hyperpolarized xenon can be done using conventional techniques, and a detailed description is omitted as not being critical to understanding the present invention.

Figure 3:
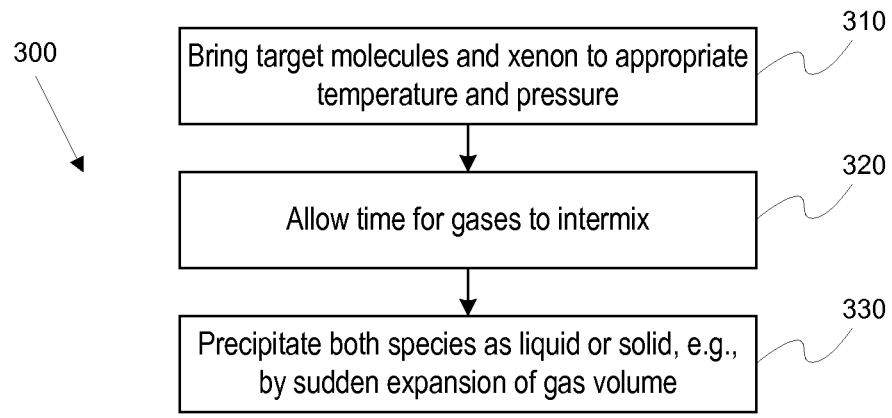
FIG. 3 is a flow diagram of a process for gas-phase mixing of a source isotope and a target according to an embodiment of the present invention

In some embodiments, mixing can occur in the gas phase. FIG. 3 is a flow diagram of a process 300 for gas-phase mixing according to an embodiment of the present invention. At step 310, the target molecules and the xenon are brought to an appropriate temperature and pressure at which both are in the gas phase. At step 320, sufficient time is allowed for the gases to intermix, and at step 330 the mixture is quickly cooled to the solid state.

Process 300 can be used in instances where the target species has sufficient vapor pressure to coexist in a suitable ratio with Xe at a practical temperature and pressure. A similar process can be used where the target species exists as a component of suspended particles that serve as condensation nuclei. These particles may be surrounded by condensed Xe by precipitating both species as liquid or solid "snow". Sudden expansion of the gas volume is one method for initiating this phase change.

Figure 4:
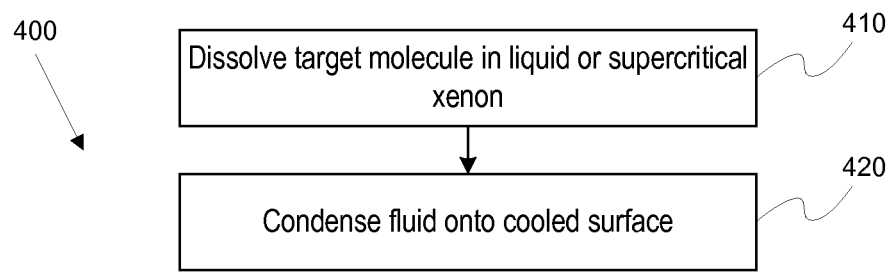
FIG. 4 is a flow diagram of a process for fluid-phase mixing of a source isotope and a target according to an embodiment of the present invention.

FIG. 4 is a flow diagram of an alternative process in which the mixture is created in a liquid state by dissolving the target molecules in liquid or supercritical xenon (step 410) and then rapidly freezing the mixture (step 420). Such a process is suitable, e.g., for small non-polar target molecules that are soluble in liquid xenon, e.g., at the level of several percent, and may also be used with other molecules that are soluble in supercritical xenon. The concentration of the solution can be optimized to provide nanoscale mixing (e.g., substantially all of the target molecules within 10 nm of a xenon) while keeping the quantity of hyperpolarized xenon within the limits of currently known production processes. A similar process can be used for fluid (e.g., liquid, gas or supercritical) mixtures of xenon with target molecules even if the target molecule is not actually dissolved in the xenon.

Freezing of these fluid mixtures to a solid needs to be fast enough to prevent phase separation on the length scale of ~10 nm or greater, as greater separation might prevent adequate mixing for spin diffusion to be effective. In one embodiment, transformation to the solid state can be achieved by directing the homogeneous fluid phase onto a colder surface, effecting a sudden reduction in temperature. Care must be taken to enforce a sharp gradient of temperature in order to prevent the deposition of the target molecule and Xe on different surfaces. A snow of hyperpolarized Xe or a surface coated with same are possible choices, but diverse cooled materials, especially those with few nuclear spins to dilute the spin polarization, are also possibilities.

When fluids condense on a cold surface, the enthalpy change across the phase transition(s) appears as heat, which must be removed to continue to produce the desired rigid solid. Thus, the condensation surface is preferably actively cooled to maintain its temperature during deposition of the fluid.

In addition, as the solid thickens on the surface, thermal conductivity to the cold surface decreases, which will eventually slow solidification. (The thermal conductivity of the condensed fluids contemplated herein is typically lower than for crystalline material, since the solid will be typically amorphous and in some cases porous.) This impediment to cooling becomes detrimental if the rise in temperature allows sufficient molecular diffusion that Xe and the target molecule separate into domains that are no longer in effective contact when they are frozen. Keeping the mole fraction of Xe high helps limit such separation, but at the cost of reducing productive throughput. Another potential loss of efficiency occurs if sufficient time is spent in a phase intermediate between the fluid and the rigid solid for spin-lattice relaxation to destroy appreciable magnetization.

Figure 5:
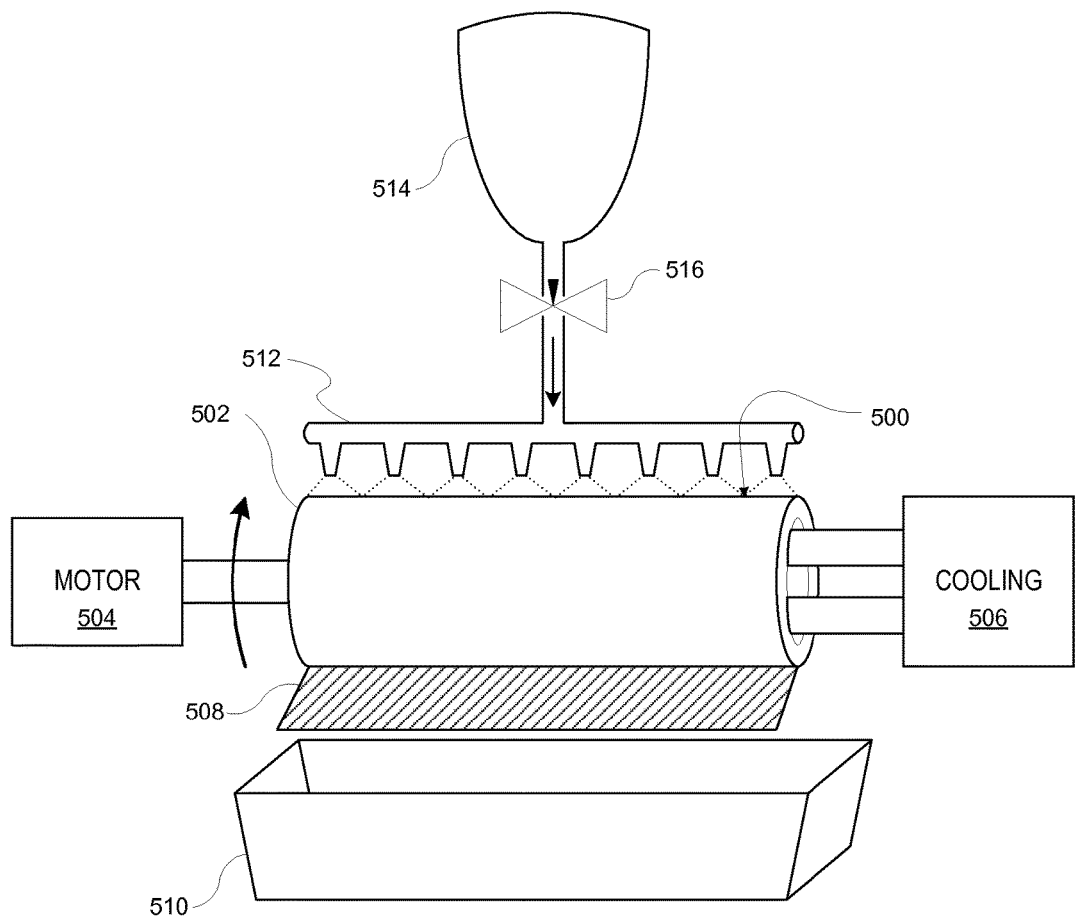
FIG. 5 is a simplified view of an apparatus that can be used in connection with the process of FIG. 4 according to an embodiment of the present invention.

Both of these problems related to low thermal conductivity may be minimized by limiting the thickness of the deposited mixture. For example, a larger cooled area would allow a thinner layer of fluid to be used for a given quantity of mixture. Another solution entails recycling of the cooled surface. For example, as shown in FIG. 5, a cooled surface can be the exterior surface 500 of a rotatably mounted cylinder 502 driven by a motor 504. A cooling system 506 is provided to continually cool cylinder 502 such that surface 500 is maintained a temperature (e.g., 25 K) at which the fluid will rapidly freeze. Cooling system 506 can continuously or periodically circulate a coolant (e.g., helium gas vaporized from liquid helium or cooled by a closed cycle refrigerator) to maintain surface 500 at the desired temperature. A scraper 508, which can be any suitably edged device with a low adhesion to the xenon-target mixture, is mounted such that its edge contacts surface 502 at a bottom point, and a collection container 510 is positioned below cylinder 502. Surface 500 can be specified to mate accurately (e.g., within 10 nm) with a scraper 508 so as to remove deposited material and expose the cooled surface for further deposition.

A distribution system 512 positioned above surface 500 distributes the mixture onto surface 500. Distribution system 512 can include, e.g., a tube with a series of holes or nozzles, or the like. Mixture 500 can be stored in vessel 514, which can be, e.g., a Teflon bag at atmospheric pressure that holds the mixture in a fluid state (e.g., gas or liquid). Valve 516 (e.g., a needle valve) can be provided to control the rate of flow of the mixture from vessel 514 into distribution system 512.

Optimum rates of deposition can be found by reducing the flow rate of the mixture and/or the temperature until the deposition occurs predominantly in the area of the cylinder targeted by the nozzle (in other words, where the sticking coefficient is close to unity). Further reduction in temperature can be made until the efficiency of polarization transfer is acceptable. Deposition at 25 K of 0.2 micromole of Xe (along with a lesser amount of the target species) per square centimeter of cooled targeted surface per second and scraping to refresh the surface at a frequency of 0.2 per second for 50 s is a representative practical procedure.

In operation, distribution system 512 applies the fluid mixture as a thin coating onto a portion of surface 500 that is oriented toward distribution system 512. The fluid mixture rapidly freezes without substantial phase separation. Cylinder 502 rotates, and as the coated portion passes scraper 508, the frozen mixture is scraped off into collection container 510. In some embodiments, cylinder 502 can rotate at a constant rate allowing for continuous coating and scraping. In other embodiments, cylinder 502 can be rotated in steps; coating of one portion of surface 500 taking place while cylinder 502 is held in position, and that portion can be scraped by rotating the cylinder. Whether the frozen mixture comes off as a single sheet or as small particles is not critical, as long as the particles contain a nanoscale mixture of xenon and target molecules. Operations to transfer spin order may be performed on deposited batches prior to scraping or on the collected sum of the material scraped.

The apparatus of FIG. 5 is illustrative, and numerous variations and modifications are possible. For example, rather than rotating the cylinder as depicted, it may be simpler to move the scraper (and optionally the collection container) around a stationary surface. Rotating the scraper while holding the cylinder stationary allows fixed connections for coolant flow to the cylinder, simplifying the design. Likewise, the spatial orientation of the system is not critical and terms such as "top" and "bottom" are used herein for convenience. Gravity, mechanical force, or a flow of non-condensing gas (e.g. helium) can be used to move the frozen mixture to the collection container. Use of a rotating or otherwise "recyclable" surface allows a larger quantity of the solid mixture to be produced with a smaller actual surface area. Since the mixing and freezing operations advantageously take place within a strong (i.e., greater than 50 mT) magnetic field, a smaller surface area provides considerable cost advantages.

Other similar processes can also be used. For example, the xenon-target mixture can be combined with precooled particles that act to provide a surface area for condensation. Optimally, the particles are added to the fluid mixture rather than adding the mixture to a volume of precooled particles. For example, a cryogenic fluid introduced as droplets can induce rapid freezing of a xenon-target fluid mixture.

A related approach for molecules that are sufficiently stable to be sublimed is to condense them simultaneously with the Xe, for example by directing an effusive beam of the target species onto a surface on which Xe is also condensing.

For some classes of molecules, such as macromolecules, neither solvation in xenon nor sublimation is likely to be entirely satisfactory. Alternative embodiments rely on other processes to achieve adequate mixing.

Figure 6:
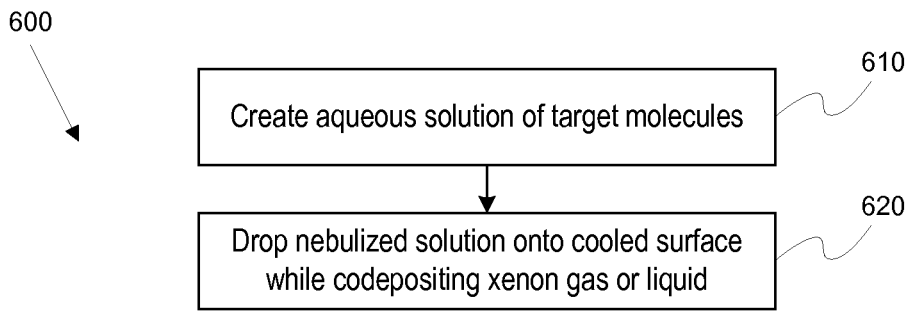
FIG. 6 is a flow diagram of a mixing process using a solution of the target molecule according to an embodiment of the present invention.

For example, FIG. 6 is a flow diagram of a process 600 according to an embodiment of the present invention that can be used for any target species that can be dissolved in water (or another non-xenon solvent). At step 610, an aqueous solution of target molecules is created. At step 620, the aqueous solution is nebulized and directed to a cooled target surface while xenon is codeposited in gas or liquid form. For example, if the target surface is in the form of a cold flat spinning disk, nebulized drops of the aqueous solution can be projected toward and dispersed across the surface by spin coating, forming nanoscale layers and mixing intimately with the codepositing xenon gas or liquid. The drop velocity and the spreading of the drop upon contact with the rotating disk followed by freezing as a thin film on the surface is a route to nanoscale mixing with the xenon condensing as a solid on the surface. As noted above, as the film thickness increases, freezing time will tend to increase, allowing more possibility of phase separation between the xenon and the target. Accordingly, the frozen film can be scraped off the surface of the disk and collected so that the coating does not reach a thickness that degrades performance.

Process 600 can provide both rapid nanoscale mixing and the ability to accumulate and store the mixture at a temperature low enough and a field high enough that spin-lattice relaxation is slow. For example, if solid xenon is held at 87 K, the resulting vapor pressure is sufficient to deposit 40 monolayers/s on a colder surface [15]. Thus, ~25 cm$^2$ of a colder surface area would be needed to make full use of a state-of-the-art output of $10^{18}$ polarized $^{129}$Xe atoms per second.

Process 600 is not limited to aqueous solutions. While water may be a desirable solvent in cases where the target is to be introduced into human or other life forms during the NMR study, solvents other than water may be substituted.

The level of solubility of the target species is not a crucial parameter in predicting the final polarization, since the spin heat capacity in this case is dominated by the xenon and water (or other solvent). Since the polarizations achieved are ~$10^4$ greater than for ordinary room temperature NMR, even molecules which are of insufficient concentration to be studied with current technology (due to low solubility or unfavorable equilibria or scarcity) are readily accessible.

Further, in most cases, it is possible to achieve mixing of xenon and the target molecule with less solvent than is desired in the final NMR solution. This smaller volume reduces the amount of hyperpolarized Xe needed per NMR aliquot. Extra solvent can be added to dissolve the mixture and bring it to the desired volume and temperature just prior to the NMR pulse sequence. Thus, many aliquots and NMR repetitions per day are feasible for most target molecules.

Figure 7:
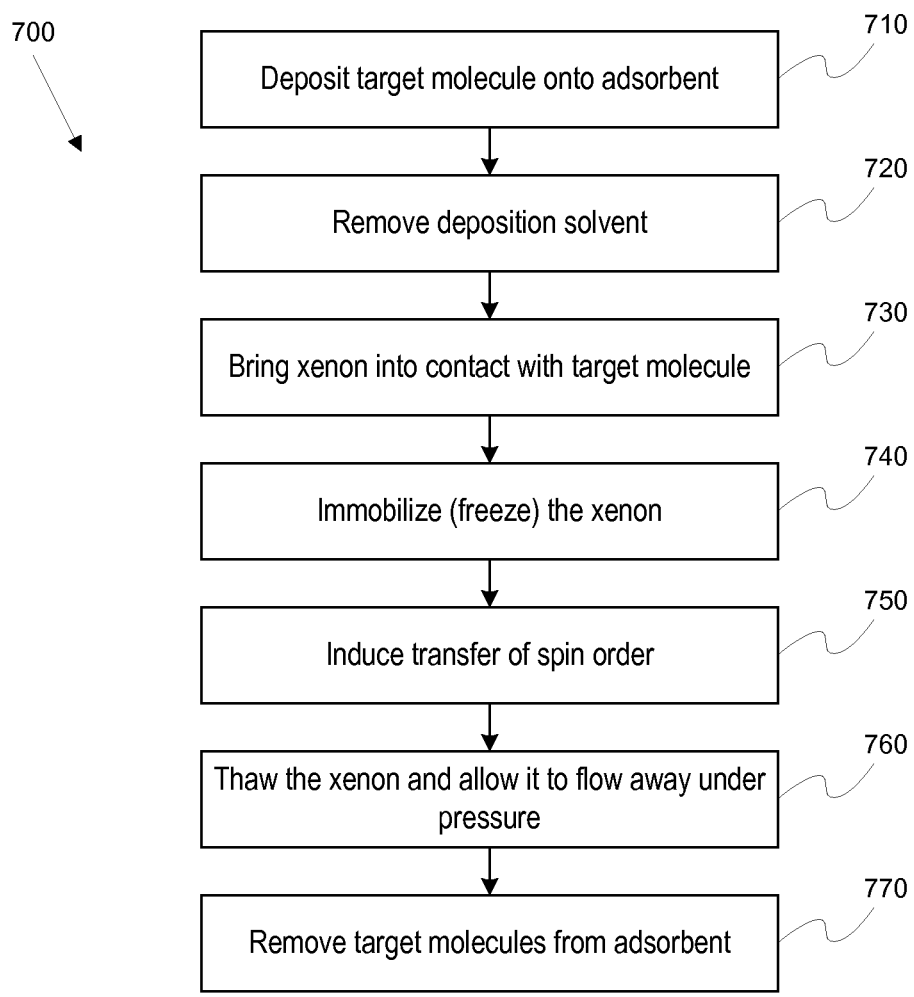
FIG. 7 is a flow diagram of a mixing process using an adsorbent according to an embodiment of the present invention.

Still other embodiments use an adsorbent to aid in immobilizing xenon and the target in nanoscale contact. FIG. 7 is a flow diagram of a representative process 700. In process 700, the contact necessary for dipolar spin coupling and subsequent separation is achieved without any requirement that the target molecule be volatile or soluble in xenon. At step 710, the target molecule is deposited onto an adsorbent, preferably a material with high surface area (e.g., a porous material), from the gas phase or from solution, e.g., using conventional solid phase extraction techniques. At step 720, the deposition solvent (if any) is removed, e.g., by flow and/or evaporation, under conditions where the target species is preferentially adsorbed, thus exposing the target on the surface of the adsorbent. At step 730, xenon is introduced, e.g., as a fluid, while the adsorbent holds the target molecules in place. At step 740, the xenon is immobilized to introduce static dipolar couplings. For example, the xenon may be briefly frozen onto the surface. At step 750, with the xenon immobilized, spin-order transfer is induced. Thereafter, at step 760 the xenon is thawed and allowed to flow away, e.g., under pressure; dielectric heating could be used to supplement thermal diffusion in this step. The xenon that flows away can be collected and recycled if desired. Finally, at step 770, the target molecule can be removed from the adsorbent, e.g., by washing the target molecules off the adsorbent material with a solvent under conditions where surface adsorption is energetically unfavorable or at least rapidly reversible. The solvent may be selected such that the resulting solution is ready for immediate introduction into the NMR subject.

The strategy in one embodiment is to cool the adsorbent column holding the target in place to ~163 K, at which temperature xenon is a liquid with a vapor pressure of ~0.9 bar. In the preferred procedure, gaseous Xe (~170 K) is condensed into the pore volume of the evacuated adsorbent. At the ~0.5 liter/hour Xe production rate currently achievable, several monolayers will condense in a few minutes. If the spin-lattice relaxation of the immobilized target species is due almost entirely to fluctuating dipole-dipole interactions with the liquid Xe, then cross relaxation may polarize the target to a useful level. This strategy of relying on polarization of the immobilized target by way of collisions with a hyperpolarized liquid is more effective for $^3$He (including mixtures with $^4$He) than for $^{129}$Xe, because of the former's greater magnetic dipole and lower liquid state temperature. Low temperature diminishes unwanted motions of the target molecule and thus diminishes those spin relaxation rates tending to drive the target polarization to the thermal equilibrium value. More typically, solid-state interactions will be needed for efficient polarization. Freezing of the adsorbed xenon can be achieved in at most seconds by chasing the xenon with a colder gas (e.g. $N_2$).

In an alternative strategy, liquid Xe can be forced into the pore volume under a pressure difference. The entirety of the volume of the pores (~0.05 cm$^3$ in some embodiments) could be filled with less than an hour's output of hyperpolarized Xe. The motivation for the use of liquid (rather than gas-phase) xenon is that the liquid range of Xe is only a few degrees, which makes it possible that condensation of xenon onto the adsorbent at a given temperature might lead to a low density gas phase or a solid phase that could block the pores and prevent the Xe from reaching all the target molecules. If the pores are simply first filled with liquid Xe, then freezing is readily achieved by lowering the surrounding temperature several degrees. Having the pores filled with liquid xenon can also provide better thermal conductivity to achieve freezing expeditiously. Alternatively (or in addition) a pressure jump of ~100 atm is effective in raising the melting point of pure Xe by several degrees, inducing freezing suddenly throughout the adsorbent volume, even before the heat from the phase transition is removed.

An alternative geometry for the adsorbent surface in such a procedure is the interior walls of nanochannels in an array. These have the advantage that pressure differences may be imposed between the two ends of each channel to speed the delivery and removal of the Xe. Further, an array of nanochannels can improve uniformity relative to naturally porous materials, particularly if the same adsorbent is reused to create multiple hyperpolarized samples of the target.

Figure 8:
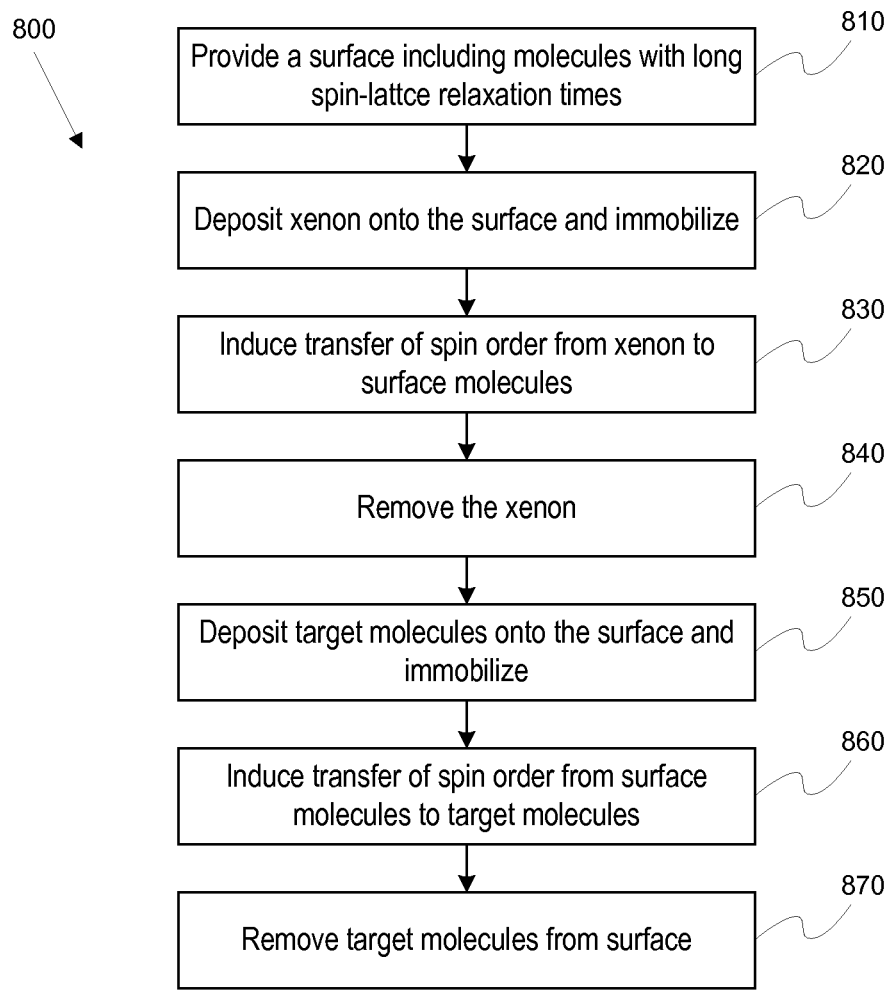
FIG. 8 is a flow diagram of a process for indirectly transferring spin order according to an embodiment of the present invention.

Still another embodiment provides an indirect approach to transferring spin order from xenon to a target. FIG. 8 is a flow diagram of a process 800 for indirectly transferring spin order according to an embodiment of the present invention. At step 810, an intermediate surface is provided. This surface advantageously incorporates atoms and/or molecules with slow spin-lattice relaxation. At step 820, xenon is deposited onto the surface and immobilized. At step 830, spin order is transferred from the xenon to the surface molecules (e.g., through thermal mixing achieved by reducing the magnetic field), and at step 840, the xenon is removed. At step 850, target molecules are deposited onto the surface and immobilized. At step 860, a transfer of spin order from the surface to the target molecules is induced. At step 870, the target molecules are removed from the surface for use in NMR applications. In process 800, the xenon and the target do not come into nanoscale contact. In alternative embodiments, any molecular structure that can be conveniently hyperpolarized may replace the role of xenon as a fluid, and a surface hyperpolarized by other techniques may replace the surface hyperpolarized by xenon.

While the invention has been described with respect to specific embodiments, one skilled in the art will recognize that numerous modifications are possible. For example, any other isotope capable of being hyperpolarized can be substituted for the xenon described herein; one such isotope would be $^3$He. Any such isotope can be used as a "source" of spin order in the processes described above. The target molecule can be any molecular species of interest for NMR studies, including but not limited to molecules containing $^{13}$C, $^{15}$N, $^1$H, or other isotopes. Further, the term "target molecules" is contemplated as including single-atom targets. Apparatus described herein can similarly be modified; shapes, dimensions, materials, and the like are all illustrative. Similarly, process conditions (temperatures, pressures, etc.) can be varied depending on the particular species involved.

Thus, although the invention has been described with respect to specific embodiments, it will be appreciated that the invention is intended to cover all modifications and equivalents within the scope of the following claims.

REFERENCES

The numbers in square brackets in the present disclosure correspond to the following publications, the contents of which are incorporated herein by reference for all purposes.

[1] Bowers, C. R.; Weitekamp, D. P. *Physical Review Letters* 1986, 57, 2645-2648.

[2] Bowers, C. R.; Weitekamp, D. P. *Journal of the American Chemical Society* 1987, 109, 5541-5542.

[3] Bhattacharya, P.; Harris, K.; Lin, A. P.; Mansson, M.; Norton, V. A.; Perman, W. H.; Weitekamp, D. P.; Ross, B. D. *Magnetic Resonance Materials in Physics Biology and Medicine* 2005, 18, 245-256.

[4] Golman, K.; Axelsson, O.; Johannesson, H.; Mansson, S.; Olofsson, C.; Petersson, J. S. *Magnetic Resonance in Medicine* 2001, 46, 1-5.

[5] Golman, K.; Ardenaer-Larsen, J. H.; Petersson, J. S.; Mansson, S.; Leunbach, I. *Proceedings of the National Academy of Sciences of the United States of America* 2003, 100, 10435-10439.

[6] Bhattacharya, P.; Weitekamp, D. P.; Harris, K.; Lin, A. P.; Ross, B. D. *European Society of Magnetic Resonance in Medicine and Biology* 2004.

[7] Johannesson, H.; Axelsson, O.; Karlsson, M. 2004, 5, 315-324.

[8] Abragam, A.; Goldman, M. *Reports on Progress in Physics* 1978, 41, 395-467.
[9] Ardenkjaer-Larsen, J. H.; Fridlund, B.; Gram, A.; Hansson, G.; Hansson, L.; Lerche, M. H.; Servin, R.; Thaning, M.; Golman, K. *Proc Natl Acad Sci USA* 2003, 100, 10158-63.
[10] Johansson, E.; Mansson, S.; Wirestam, R.; Svesson, J.; Petersson, S.; Golman, K.; Stahlberg, F. *Magnetic Resonance in Medicine* 2004, 51, 464-472.
[11] Golman, K.; in't Zandt, R.; Thaning, M. *Proceedings of the National Academy of Sciences of the United States of America* 2006, 103, 11270-11275.
[12] Golman, K.; in't Zandt, R.; Lerche, M.; Pehrson, R.; Ardenkjaer-Larsen, J. H. *Cancer Research* 2006, 66, 10855-10860.
[13] Ishii, M.; Emami, K.; Kadlecek, S.; Petersson, J. S.; Golman, K.; Vandat, V.; Yu, J. S.; Cadman, R. V.; MacDuffie-Woodburn, J.; Stephen, M.; Lipson, D. A.; Rizi, R. R. *Magnetic Resonance in Medicine* 2007, 57, 459-463.
[14] Joo, C. G.; Hu, K. N.; Bryant, J. A.; Griffin, R. G. *Journal of the American Chemical Society* 2006, 128, 9428-9432.
[15] Gerhard, P.; Koch, M.; Jansch, H. J. *Comptes Rendus Physique* 2004, 5, 297-304.
[16] Gatzke, M.; Cates, G. D.; Driehuys, B.; Fox, D.; Happer, W.; Saam, B. *Physical Review Letters* 1993, 70, 690-693.
[17] Happer, W. *Reviews of Modern Physics* 1972, 44, 169-250.
[18] Happer, W.; Miron, E.; Schaefer, S.; Schreiber, D.; Vanwijngaarden, W. A.; Zeng, X. *Physical Review A* 1984, 29, 3092-3110.
[19] Walker, T. G.; Happer, W. *Reviews of Modern Physics* 1997, 69, 629-642.
[20] Ruth, U.; Hof, T.; Schmidt, J.; Fick, D.; Jansch, H. *J. Applied Physics B-Lasers and Optics* 1999, 68, 93-97.
[21] Zook, A. L.; Adhyaru, B. B.; Bowers, C. R. *Journal of Magnetic Resonance* 2002, 159, 175-182.
[22] Ruset, I. C.; Ketel, S.; Hersman, F. W. *Physical Review Letters* 2006, 96.
[23] Driehuys, B.; Cates, G. D.; Miron, E.; Sauer, K.; Walter, D. K.; Happer, W. *Applied Physics Letters* 1996, 69, 1668-1670.
[24] Ruset, I. C.; Kettel, S.; Hersman, F. W. *Experimental NMR Conference, Asilomar, California* 2004.
[25] Hartmann, S. R.; Hahn, E. L. *Physical Review* 1962, 128, 2042-2053.
[26] Pines, A.; Gibby, M. G.; Waugh, J. S. *Journal of Chemical Physics* 1973, 59, 569-590.
[27] Long, H. W.; Gaede, H. C.; Shore, J.; Reven, L.; Bowers, C. R.; Kritzenberger, J.; Pietrass, T.; Pines, A.; Tang, P.; Reimer, J. A. *Journal of the American Chemical Society* 1993, 115, 8491-8492.
[28] Abragam, A.; Proctor, W. G. *Physical Review* 1958, 109, 1441-1458.
[29] Navon, G.; Song, Y. Q.; Room, T.; Appelt, S.; Taylor, R. E.; Pines, A. *Science* 1996, 271, 1848-1851.
[30] Sauer, K. L.; Fitzgerald, R. J.; Happer, W. *Chemical Physics Letters* 1997, 277, 153-158.
[31] Fitzgerald, R. J.; Sauer, K. L.; Happer, W. *Chemical Physics Letters* 1998, 284, 87-92.
[32] Driehuys, B.; Cates, G. D.; Happer, W.; Mabuchi, H.; Saam, B.; Albert, M. S.; Wishnia, A. *Physics Letters A* 1993, 184, 88-92.
[33] Bowers, C. R.; Long, H. W.; Pietrass, T.; Gaede, H. C.; Pines, A. *Chemical Physics Letters* 1993, 205, 168-170.
[34] Cherubini, A.; Payne, G. S.; Leach, M. O.; Bifone, A. *Chemical Physics Letters* 2003, 371, 640-644.
[35] H. Gaede, *NMR of surfaces and interfaces using spin polarized xenon*. Ph.D. thesis, Chemistry, University of California, Berkeley, 1995.
[36] J. S. Lee, and A. K. Khitrin, Adiabatic cross-polarization via intermediate dipolar-ordered state. *Journal of Magnetic Resonance* 2005, 177, 152-154.
[37] Golman, K.; Ardenkjaer-Larsen, J. H.; Svensson, J.; Axelsson, O.; Hansson, G.; Hansson, L.; Johannesson, H.; Leunbach, I.; Mansson, S.; Petersson, J. S.; Pettersson, G.; Servin, R.; Wistrand, L. G. *Academic Radiology* 2002, 9 Suppl 2, S507-10.
[38] Frydman, L.; Scherf, T.; Lupulescu, A. *Proceedings of the National Academy of Sciences of the United States of America* 2002, 99, 15858-15862.
[39] Goldman, M.; Johannesson, H.; Axelsson, O.; Karlsson, M. *Magnetic Resonance Imaging* 2005, 23, 153-157.
[40] M. Carravetta, and M. H. Levitt, Long-Lived Nuclear Spin States in High-Field Solution NMR. *Journal of the American Chemical Society* 2004 126, 6228-6229.
[41] Haake, M.; Goodson, B. M.; Laws, D. D.; Brunner, E.; Cyrier, M. C.; Havlin, R. H.; Pines, A. *Chemical Physics Letters* 1998, 292, 686-690.

What is claimed is:

1. A method for preparing target molecules in a hyperpolarized state, the method comprising:
   creating a solid nanoscale mixture of hyperpolarized source isotopes with target molecules of a target molecular species, wherein the hyperpolarized source isotopes comprise xenon and wherein creating the solid nanoscale mixture includes:
   depositing the target molecules onto an adsorbent surface;
   introducing the xenon as a fluid onto the target molecules and the adsorbent surface; and
   immobilizing the xenon to a solid state;
   inducing a transfer of spin order from the hyperpolarized source isotopes to the target molecules within the solid mixture while the xenon is immobilized, thereby establishing a hyperpolarized state of the target molecules; and
   removing the hyperpolarized source isotopes from the mixture while maintaining the target molecules in the hyperpolarized state.

2. The method of claim 1 wherein immobilizing the xenon includes freezing the xenon.

3. The method of claim 1 wherein immobilizing the xenon includes increasing the pressure to force the fluid xenon into pores of the adsorbent surface, then decreasing the temperature to freeze the xenon.

4. The method of claim 1 further comprising:
   after inducing the transfer of spin order, removing the xenon while leaving the target molecules on the adsorbent surface.

5. The method of claim 4 wherein the adsorbent surface includes an interior wall of a nanochannel and wherein a pressure differential along the length of the nanochannel is imposed during the acts of introducing and removing the xenon to increase the rate of movement of the xenon.

6. A method for conducting a nuclear magnetic resonance (NMR) experiment on a subject, the method comprising:
   creating a solid nanoscale mixture of target molecules of a target molecular species and hyperpolarized source isotopes, wherein the hyperpolarized source isotopes comprise xenon and wherein creating the solid nanoscale mixture includes:

depositing the target molecules onto an adsorbent surface;

introducing the xenon as a fluid onto the target molecules and the adsorbent surface; and immobilizing the xenon to a solid state;

inducing a transfer of spin order from the hyperpolarized source isotopes to the target molecules while the xenon is immobilized, thereby establishing the target molecules in a hyperpolarized state;

separating the source isotopes from the hyperpolarized target molecules;

introducing the hyperpolarized target molecules into the subject; and performing an NMR measurement on the subject, wherein the NMR measurement includes detecting a signal corresponding to an isotope included in the target molecular species.

7. The method of claim 6 wherein separating the source isotopes from the hyperpolarized target molecules includes warming the solid mixture such that the xenon-sublimates while the target molecules remain in a hyperpolarized state.

8. The method of claim 6 wherein separating the source isotopes from the hyperpolarized target molecules includes crushing the mixture to promote sublimation of the xenon.

9. The method of claim 6 wherein introducing the hyperpolarized target molecules into the subject includes injecting the target molecules into the subject.

10. The method of claim 6 wherein the subject is living and introducing the hyperpolarized target molecules into the subject includes causing the subject to inhale the hyperpolarized target molecules.

11. The method of claim 6 wherein introducing the hyperpolarized target molecules into the subject includes adsorption of the target molecules into a tissue of the subject.

12. The method of claim 6 wherein:

separating the source isotopes from the hyperpolarized target molecules includes dissolving the mixture in a liquid solvent to create a solution containing the target molecules; and introducing the hyperpolarized target molecules into the subject includes injecting the subject with the solution.

13. The method of claim 12 wherein the xenon bubbles out of the solution during dissolving of the mixture.

14. The method of claim 6 wherein a mole fraction of the hyperpolarized source isotopes in the nanoscale mixture is sufficiently large that a spin temperature of the nanoscale mixture approximates an initial spin temperature of the hyperpolarized source isotopes when the nanoscale mixture is created.

15. The method of claim 2 wherein the xenon is frozen at a temperature of not more than 77 K.

16. The method of claim 2 wherein the xenon is frozen at a temperature of about 25 K.

17. The method of claim 1 wherein inducing the transfer of spin order includes varying a magnetic field in a region containing the solid nanoscale mixture.

18. The method of claim 17 wherein varying the magnetic field includes providing a high magnetic field in the region containing the solid nanoscale mixture and applying a radio-frequency pulse sequence in the magnetic field.

19. The method of claim 17 wherein varying the magnetic field includes reducing the magnetic field in the region containing the solid nanoscale mixture to a low value, then restoring the magnetic field.

20. The method of claim 1 wherein the source isotopes comprise $^{129}$Xe.

21. The method of claim 1 wherein the target molecular species is a molecule that includes at least one of a $^{13}$C atom, a $^{15}$N atom, or a $^{1}$H atom.

22. The method of claim 1 further comprising:

storing the solid nanoscale mixture under temperature and magnetic-field conditions such that the spin order of the solid nanoscale mixture relaxes slowly.

\* \* \* \* \*